United States Patent [19]

White

[11] Patent Number: 4,959,466

[45] Date of Patent: Sep. 25, 1990

[54] PARTIALLY ESTERIFIED POLYSACCHARIDE (PEP) FAT SUBSTITUTES

[75] Inventor: John F. White, Summit, N.J.

[73] Assignee: Arco Chemical Technology, Inc., Wilmington, Del.

[21] Appl. No.: 147,806

[22] Filed: Jan. 25, 1988

[51] Int. Cl.$^5$ .................. C07H 13/00; C08B 31/00; C08B 35/00; A23D 7/00

[52] U.S. Cl. .................... 536/119; 536/56; 536/102; 536/2; 536/3; 536/114; 536/58; 536/60; 536/107; 426/603; 426/804

[58] Field of Search .............. 426/603, 804; 536/119, 536/56, 102, 2, 3, 114, 58, 60, 107

[56] References Cited

U.S. PATENT DOCUMENTS

| | | | |
|---|---|---|---|
| 3,023,104 | 2/1962 | Battisia et al. | 426/601 |
| 3,600,186 | 8/1971 | Mattson et al. | 426/611 |
| 4,061,610 | 12/1977 | Glowaky et al. | 536/110 |
| 4,247,568 | 1/1981 | Carrington et al. | 426/804 |
| 4,304,768 | 12/1981 | Staub et al. | 514/54 |
| 4,536,408 | 8/1985 | Morehouse et al. | 426/603 |
| 4,797,300 | 1/1989 | Jandacek et al. | 536/119 |

FOREIGN PATENT DOCUMENTS

| | | | |
|---|---|---|---|
| 55-71446 | 5/1980 | Japan | 426/603 |
| 59-210025 | 11/1984 | Japan | 426/607 |
| 0156698 | 8/1985 | Japan | 536/119 |
| 2193221 | 2/1988 | United Kingdom . | |

OTHER PUBLICATIONS

Roy L. Whistler et al, Industrial Gums-Polysaccharides and Their Derivatives, 1973, pp. 443 & 444.

Primary Examiner—Ronald W. Griffin
Assistant Examiner—Everett White
Attorney, Agent, or Firm—Jacques M. Dulin

[57] ABSTRACT

Partially esterified oligosaccharides and polysaccharides (PEPs) of the formula $[P-O-R)_x]_n$, where P is a polysaccharide having $n=3-50$ (preferably 3-10) $C_4$-$C_8$ saccharide units, y is 0–4 (preferably 1 or 2), R is H or a $C_3$-$C_{28}$ acyl group, and x is the degree of esterification ranging from 1–80 percent. The PEPs are used as indigestible fat substitutes (fat mimetics). They have non-caloric food values, with good organoleptic characteristics, are substantially resistant to intestinal absorption and do not appreciably hydrolyze in the digestive tract. Suitable polysaccharides are preferably selected from xanthan gum, guar gum, gum arabic, aliginates, cellulose hydrolysis products, hydroxypropyl cellulose, starch hydrolysis products, casein, Karaya gum and pectin. $C_5$ and $C_6$ oligosaccharides of $n=3-10$ units are preferred. The polysaccharides are transesterified with fatty acid methyl esters to create PEPs of a degree of esterification determined for each polysaccharide. The physical properties of the resultant PEPs range from a liquid oil, through fats, greases, and ultimately to waxes, and are useful in food formulations and for cooking as they have good mouth feel and characteristics similar to vegetable oils and fats. Being relatively non-absorbable, indigestible, and non-toxic they may be substitued for natural or processed oils and fats, while maintaining low caloric value.

20 Claims, No Drawings

PARTIALLY ESTERIFIED POLYSACCHARIDE (PEP) FAT SUBSTITUTES

FIELD

This invention relates to partially esterified polysaccharides (PEPs) of the general formula $[P—O(R)_x]_n$ having $n > 2$ $C_4$-$C_8$ saccharide units and a degree of esterification, $x$, in the range of 1–80%, and their use as indigestible, non-caloric fat substitutes (fat mimetics) for cooking and in food compositions. The PEPs have good organoleptic characteristics and may have physical properties ranging from a liquid oil through fats to greases. They are useful in food formulations and cooking as they have good "mouth feel" and characteristics similar to vegetable oils and fats. Being relatively non-absorbable, indigestible, and non-toxic they may be substituted for natural or processed oils and fats, while offering the advantage of low caloric value.

BACKGROUND

The accumulation of medical evidence in recent years regarding the adverse health implications of high fat diets, principally heart attacks, atherosclerosis and overweight, has created a heightened consumer awareness and concern of diet and caloric intake. Common obesity is one of the most prevalent metabolic disorders afflicting people today. It is estimated that between 70–80% of U.S. adult females follow a weight reducing diet at least once a year. The concerns of both men and women have given rise to diet fads, diet drinks (most noticeably in the soft drink, wine and beer industry), exercise programs and health clubs.

Although fats and oils are necessary for balanced nutrition, the average consumer simply ingests more than is required for proper nutrition. Fat, at 9 calories per gram, as compared to carbohydrates or proteins, at 4 calories per gram, is the most concentrated dietary energy form. It is estimated that fat constitutes approximately 40% of the total calories found in the typical western diet. Fats are consumed directly from meats, spreads, salad oils, and natural produce such as nuts and avocados. Fats and oils are consumed as a result of absorption or incorporation in the foods during baking and frying. The dramatic rise in popularity of "fast foods" in the U.S. has been a major contributor to the increase in the consumption of dietary fat since fast foods rely extensively on the frying process. In addition, the snack food industry uses large amounts of fats and oils in the production of potato chips, corn chips and other snack items. For example, in 1981 the USDA estimated approximately 12 billion pounds of fat and oil were used in edible products, predominately baking, frying fats, margarine, salad oil and/or cooking oil.

Many nutritionists believe that Americans typically rely on fats for a disproportionately large percentage of calories in their diet. The National Research Council, for example, has recommended that Americans reduce the proportion of their dietary calories coming from fats from 40% to at least 30%. Clearly an enormous potential exists in the health food industry for a fat substitute of fat mimetic that is either entirely indigestible, or has reduced caloric value. Replacement of fats in the diet with non-caloric substitutes is a more efficient means of reducing caloric intake than replacement of sugar or carbohydrates. In fact, gram for gram, the substitution of a fat mimetic into the diet is more than twice as effective than the reduction of carbohydrate content through the introduction of saccharine or Nutra-sweet.

One difficulty in eliminating fat from the diet comes from the fact that fats and oils are all-pervasive in modern food products. In part, this is because they play an important role in the organoleptic acceptability of food products. Consequently, fat mimetics must have good organoleptic qualities of mouth feel and be tasteless. Related to the aesthetic organoleptic qualities desired in a fat mimetic, substitutes must also have appropriate physical properties for use in food compositions. That is, they should be liquids or solids depending on whether they are used as oil or shortening substitutes. Where used for cooking, mimetics must be thermally stable. For example, while certain polysaccharide gums have been used as thickening agents, bulking agents or fillers in low-calorie foods, they can give a product a "slimy" mouth feel and are unsuitable for cooking as they have no thermal stability.

For a fat mimetic to be used as an acceptable substitute, it must be indigestible, that is, not hydrolyzed in the digestive tract, as well as unable to be directly absorbed through the intestinal wall. While some types of fat substitutes may be indigestible, they are not of sufficiently high molecular weight to prevent them from being absorbed through the intestinal wall. The threshold molecular weight of non-absorbability for lipophilic molecules appears to be about 600 amu.

The fat substitute must itself be non-toxic at high levels of ingestion. It must contain no toxic residues or impurities. To the extent that a fat substitute may be partially hydrolyzed in the digestive tract, any by-products of the hydrolysis must be non-toxic and/or capable of being metabolized. If the by-products are to be metabolized, they should have very low caloric value. In general, fat substitutes must be without any serious medical side affects.

Acceptable synthetic fats would be added in large quantities (30–60%) to salad oils, cooking oils, margarines, butter blends, mayonnaise, shortenings and the like to create a new class of low-calorie products. While "low calorie" mayonnaise and salad dressings are presently available, the reduction in calories is achieved by increasing the water content with a corresponding loss in the organoleptically "rich" taste of such products. The use of an effective fat mimetic would not require such a trade-off.

A current review of the field is found in a feature article entitled *"Gettinq The Fat Out - Researchers Seek Substitutes For Full-Fat"* JAOCS, Vol. 63, No. 3, (March 1986) pp. 278–286, 288. The article stresses the need to identify satisfactory means of reducing dietary fat intake stating that although media and various U.S. departments have recommended a decrease in consumption, actual per capita consumption has increased. Several methods for reducing dietary fat intake, including the use of fat substitutes, are discussed. Sugar polyesters, sucrose esters and branched polysaccharides are mentioned among the possible candidates for fat substitutes.

One prior art proposed fat substitute is sucrose polyester (SPE), shown in U.S. Pat. Nos. 3,600,186 (Matson, et al., 1971), 3,521,827 and 3 963,699 (Rizzi, et al., 1976) of Proctor & Gamble. The SPEs are produced by the reaction of a monosaccharide, disaccharide or sugar alcohol having a minimum of four hydroxyl groups with fatty acids having from 8–22 carbon atoms. It was reported in "Chemical and Engineering News" (July 26, 1982, page 32) that incorporating SPE as a partial replacement of the fats in the diets of ten obese patients dropped their caloric intake while satisfying their perceived need for fats. An additional benefit was the lowering of serum cholesterol, low density lipo-protein and triglycerides, all of which have been implicated in artery hardening diseases. However, SPE has the serious disadvantage of causing diarrhea, and plasma vitamin A and vitamin E levels are decreased.

Pat. No. 3,251,827 (Schnell et al.) discloses a preparation of SPE by means of a solvent-free interesterification using phenyl esters. However, phenol is liberated during the reaction. Since phenol is extremely toxic and caustic, it contaminates the product and is very difficult to separate. Accordingly, this process did not prove satisfactory for synthesis of SPEs for the food industry.

Some fatty acid esters of amylose, a very high polymer water soluble polysaccharide component of starch, have been synthesized and demonstrated to have many of the qualities necessary to make them low calorie synthetic fats [J. AM. Oil Chem. Soc., 39, 19 (1962) and 40, 551 (1963)]. These esters are only partially hydrolyzed and, in addition, only the fatty acid portion is absorbed through the intestinal wall making the caloric value of the materials very low.

Pat. No. 3,963,699 calls for solvent-free transesterification involving heating a mixture of a polyol containing four hydroxyls, a fatty acid lower alkyl ester, and an alkali metal fatty acid soap in the presence of a basic catalyst to form a homogenous melt, and subsequently adding excess fatty acid lower alkyl esters to the reaction product of that heated mixture to obtain the SPE. The polyol is any aliphatic or aromatic compound containing at least two free hydroxyl groups.

The need for low caloric fat-containing food compositions is also recognized in U.S. Pat. No. 3,579,548 (Whyte, 1971) of Proctor and Gamble, which discloses uses of triglyceride esters of alpha-branched carboxylic acids as low calorie fats. It is postulated that the alpha-branched carboxylate structure prevents the compounds from being hydrolyzed by pancreatic enzymes. Proposed uses are as fat replacements in salad oil, mayonnaise, margarine and dairy products.

U.S. Pat. No. 3,158,490 (Baur and Lutton, 1964) describes noncloudy salad oil containing esters of disaccharides in which there are not more than five unesterified hydroxy groups.

U.S. patent 4,034,083 (Matson, 1977) also to Proctor and Gamble discloses fortification of the SPEs with fat-soluble vitamins to form pharmaceutical compositions for treating or preventing hyper- cholesterolemia in animals, and for use in low calorie foods. This mixture is required because SPE ingestion alone causes vitamin depletion as noted above. Booth, A., and Gros, A., in a paper entitled Caloric *Availability and Digestibility of New-Type Fats,* Journal of the American Oil Chemists Society, Vol. 40, October 1963, pp. 551–553, disclose that in rat feeding studies amylose palmitate, amylose stearate and amylose oleate are only 17–29% digested. A related prior paper of Gros, A., and Feuge, R., entitled *Properties of the Fatty Acid Esters of Amylose.* Journal of the American Oil Chemists Society, Vol. 39, January 1962, pp. 19–24 discloses that these esters do not have sharp melting points and are extremely viscous when melted. The densities were somewhat greater than those of corresponding free fatty acids and glycerides. While the interest was for use as dip-type coatings in both foods and non-foods, no information appears to be available concerning the ability of these compounds to mimic sensory and functional properties of triglyceride fats in foods.

Canadian Pat. No. 1,106,681 (Trost, 1981) issued to Swift and Company relates to dialkyl glycerol ethers which are only absorbed in small amounts when fed to rats. Blends are said to exhibit the physical and organoleptic properties of conventional fats.

U.S. Pat. No. 2,962,419 (Minich, 1960), discloses esters of neopentyl type alcohols such as pentaerythritoltetracaprylate. The alcohols contain from 1–8 hydroxyl radicals and include at least one neopentyl nucleus while the fatty acids contain at least four carbon atoms. They were shown to be non-hydrolyzable by pancreatic lipase. Rats fed with these esters had lower levels of lipids in there serum. However, in demand feeding studies, rats which received these neopentyl alcohol esters ate more food than the control rats and thus there was no difference in weight gain among the two groups. Accordingly, it is possible that fat craving is stimulated by these compounds rather than satisfied.

Retrofats are esters of fatty alcohols with tricarboxylic acids It is reported that they are not hydrolyzed by pancreatic lipase and thus may have potential as non-absorbable fat substitutes. However, increased stool bulk resulting from ingestion of the non-absorbable retrofats is reported to be a potential drawback.

Alkyl esters, such as dodecyl ester of 2,3-ditetradecyloxypropionic acid have been suggested as a fat substitute but were found to be metabolized and absorbed in vivo rat study experiments. The alkyl ester group was split off first, followed by the alkyl ether groups.

As reported in JACS, Vol. 8 (1958) pp. 6338 ff and JAOCS, Vol. 36 (1959) pp. 667 ff, the USDA has synthesized a number of diglyceride esters of short chain dibasic acids for potential application in foods. Distearin glyceride esters of dicarboxcylic acids were found to be poorly digested and utilized by rats. Distearin adipate was almost completely non-digested while adiposteraisn was only 58% digested in rat feeding trials. In contrast, the oleostearin and dolein esters of dicarboxylic acids were more digestible and utilized. The symmetrical diglyceride esters of fumaric, succinic and adipic acids are more viscous than cottonseed oil and coconut oil. These may have use as pan greases, slab dressings or surface coatings for foods.

It is clear that there is a great need in the art for improved fat substitutes that are not only aesthetically satisfactory, but which are both easy and inexpensive to synthesize and do not have the disadvantages or negative side-effects of the prior art proposed compounds.

THE INVENTION

Objects:

It is among the objects of this invention to provide improved indigestible fat substitutes comprising partially esterified oligosaccharides and low polymer polysaccharides (PEPs) which may be used alone as cooking oils, fats or waxes, as part of food compositions, or as a partial or total substitute for fats or oils.

It is another object of this invention to provide an indigestible, non-absorbable, non-caloric fat substitute or fat mimetic useful in food compositions or for the preparation of food.

Another object of this invention is to provide improved, substantially indigestible fat substitutes or partial substitutes, of the partially esterified oligossacharides and low polymer polysaccharides wherein the esterification index is sufficient to prevent a substantial degree of hydrolysis by pancreatic lipase;

It is another object of this invention is provide improved, substantially indigestible fat substitutes or partial substitutes, of partially esterified polysaccharides of the formula $[P\text{---}O(R)_x]_n$, wherein n, the number of $C_4$-$C_8$ saccharide units, shall be greater than 2, and is preferably an oligosaccharide of $n=3-10$;

It is another object of this invention to provide improved fat substitutes which are partially esterified oligosaccharides and polysaccharides of the formula $[P\text{---}O(R)_x]_n$, in which x, the degree of esterification, shall be between 1% and 80% depending on the selected value for each saccharide polymer;

It is another object of this invention to provide partially esterified oligosaccharides and polysaccharides in which the acyl groups are of sufficient size to prevent absorption through the walls of the digestive system, the degree of esterification is sufficiently high to prevent a substantial degree of hydrolysis, i.e. will make the particular polysaccharide indigestible, which have good organoleptic properties, and which themselves and their hydrolysis products, are non-toxic;

It is another object of this invention to provide methods of producing the fat substitutes of this invention, and preferably which can use naturally available materials such as the thickening agents now used in food including xanthan gum, guar gum, gum arabic, aliginates, cellulose and its derivatives, hydroxypropyl cellulose, casein, Karaya gum, and pectin;

It is anther object of this invention to provide improved food compositions and products employing the fat substitutes of this invention;

Still further and other objects will be evident from the specification and claims of this application.

SUMMARY

This invention comprises partially esterified oligosaccharides and relatively low polymer polysaccharides (PEPs), and their use as indigestible fat substitutes (fat mimetics) having low-caloric food values, good organoleptic characteristics, substantial resistance to intestinal absorption, and which do not appreciably hydrolyze in the digestive tract.

The PEP indigestible fat substitutes of this invention may be characterized by the general formula $[P\text{---}O(R)_x]_n$ and have the general structure:

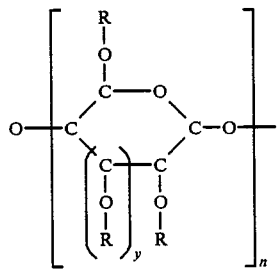

wherein P is a polysaccharide of $n>2$ $C_4$-$C_8$ saccharide units, y is 0-4, R is H or $C_3$-$C_{28}$ acyl moieties which may be the same or different in each saccharide unit, and x is the esterification factor for each PEP ranging from 1% to 80% of all R's being acyl, said index, x, being selected sufficient to prevent a substantial degree of hydrolysis by pancreatic lipase, i.e., being below about 20% as compared to olive oil. As distinct from sucrose, a dimer, the PEPs of this invention are longer chain polymers of $n=3-50$ or more units such as polysaccharide units, but preferably oligosaccharide units where $n=3-10$ saccharide units. As such they are low polymers as compared to starch or amylose.

DETAILED DESCRIPTION OF THE BEST MODE

The following detailed description illustrates the invention by way of example, not by way of limitation of the principles of the invention. This description will clearly enable one skilled in the art to make and use the invention, and describes several embodiments, adaptations, variations, alternatives and uses of the invention, including what I presently believe is the best mode of carrying out the invention.

Suitable oligo/polysaccharide materials which may be used to form the PEPs of this invention include thickening agents currently used in foods, such as: xanthan gum, guar gum, gum arabic, aliginates, cellulose and its hydrolysis products, hydroxypropyl cellulose, starch hydrolysis products where n is less than about 50, casein, Karaya gum and pectin. Esterification of these substances with fatty acids in accord with this invention will improve the organoleptic, "mouth feel" of the oligo/polysaccharide gums currently used in low-calorie foods.

The degree of esterification, x, is controlled for each polysaccharide to be sufficient to prevent a substantial degree of hydrolysis by pancreatic lipase, and depending on the alkyl chain length, may be between 1% to 80% of the available hydroxyl H's being substituted by alkyl groups, the longer the alkyl chain, the lower the value of x. The hydrophilicity of these polysaccharides can be modified depending upon the degree of esterification, the greater the degree the lesser the solubility in water. Each polysaccharide will have a selected degree of esterification of the available hydroxy groups (e.g. between 1 and 80%) which will give the ester the correct HLB (Hydrophobic/Lipophilic Balance). For example, depending on the degree of esterification of xanthan gum with palmitic acid, the ester may be water soluble, an mulsifier or water insoluble.

The acyl chain length is also selected to be of sufficient size so that by control of the degree of esterification of the available hydroxyls the resultant PEPs are resistent to digestive tract absorption and in vivo digestion by non-specific digestive or lingual lipases. One disadvantage with some of the other proposed fat substitutes is the diarrhea side-effect. The thickening and "bulking" properties of the PEPs of this invention are expected to reduce the tendency of this side-effect.

Oligo/polysaccharide gums of the type mentioned above, although now used in low-calorie foods, can give the food product a slimy "mouth feel" In contrast, the PEPs of this invention can exhibit improved "mouth feel" by virtue of selected esterification.

Olive oil, as a representative substrate, has a rate of in vitro lipase reactivity (hydrolysis) of 100. In contrast, even with an esterification index on the order of 1-5%, the PEPs of this invention can exhibit a hydrolysis rate value on the order of 20-30% of the olive oil. By non-digestibility I mean an in vitro lipase activity below about 20% as compared to olive oil.

There are two principal factors to be considered in determining the proper degree of esterification of the polysaccharide to assure non-digestibility: the length of the acyl ester chain; and the total number of hydroxyl groups available for esterification. This latter is a function of y and n as defined above. Where $n>2$, a suitable in vivo threshold for non-digestibility is the esterification of an average of about 1 hydroxyl group per saccharide unit.

It is preferred to esterify an average of one or more available hydroxyl groups per saccharide unit with one or more $C_8$–$C_{24}$ fatty acids. This produces an end product PEP with physical properties ranging from a liquid oil, through fats and greases, and ultimately to waxes. The resultant PEPs are useful in food formulations and for cooking as they have good "mouth feel" and characteristics similar to vegetable oils and fats. Being relatively non-absorbable, indigestible, and non-toxic they may be substituted for natural or processed oils and fats, but have no caloric value. Where the PEP product has a relative lipase rate below about 20 (i.e. 20% of olive oil), various amounts of the PEP fat substitute of this invention can be used in a blend with conventional fats (e.g. 90% PEP to 10% Crisco) to achieve a desired organoleptic quality or provide a particular cooking use, (e.g. oil vs. fat).

Examples of such preferred fatty acids are caprylic, capric, lauric, myristic, myristoleic, stearic, palmitic, palmitoleic, ricinoleic, linoleic, linolenic, elaeostearic, arachidic, behenic, erucic, oleic, and/or heptadecanoic acid. The fatty acids can be derived from suitable naturally occurring or synthetic fatty acids and can be saturated or unsaturated, including positional isomers, depending on the desired physical properties, e.g. liquid or solid, of the fat compound. These fatty acids are readily available. Fatty acids per se or naturally occurring fats and oils can serve as the source for the fatty acid component. For example, rapeseed oil provides a good source for $C_{22}$ fatty acid. $C_{16}$–$C_{18}$ fatty acids can be provided by tallow, soybean oil, or cottonseed oil. Shorter chain fatty acids can be provided by coconut, palm kernel oil, or babassu oils. Corn oil, fish oil, lard, olive oil, palm oil, peanut oil, safflower seed oil, sesame seed oil, jojoba oil and sunflower seed oil, are examples of other natural oils which can serve as the source of the fatty acid component. Among the fatty acids, those that are most preferred have from about 14 to about 18 carbon atoms, and preferably are selected from the group consisting of myristic, palmitic, stearic, oleic, and linoleic acids. The preferred sources for the fatty acid components are natural fats and oils which have a high concentration of these fatty acids, e.g. soybean oil, olive oil, cottonseed oil, corn oil, tallow and lard.

Even where the fatty acid moieties are hydrolyzed off the PEPs of this invention, no toxicity is expected, as both the oligo/polysaccharide gums and the fatty acids are given GRAS (Generally Recognized as Safe) status by the FDA.

Ordinary food compositions containing from about 10 to 100% of the usual fat component in the form of the PEPs of this invention may be prepared in the conventional manner of mixing or blending and cooking until the food product is adjudged "done" in the known sense. This range covers partial to full substitution of ordinary fat-type ingredients with the compounds of this invention. At the 10% level there is a partial substitution, while at the 100% level there is a full substitution. At the 100% level, for example, the PEP food product of this invention includes oils, fats and greases for cooking.

Thus, food products may be made of, or cooked in, a mixture of natural fats and the PEP synthetic fats of this invention, blended in proportion to provide any predetermined amount of fat caloric value. Depending on the organoleptic qualities desired, the amount of substitution of the PEP for natural fats would range from a few percent, to give fractional reduction in caloric value, to entire substitution for a non-caloric product. Conversely, where the PEP product has a relative lipase rate close to 20, different amounts of the PEP fat substitute of this invention could be used in the blend to achieve a desired organoleptic quality or provide a particular cooking use, (e.g., oil vs fat). Thus, the PEPs of this invention may be added to or used for salad oils, cooking oils, margarine, butter blends, mayonnaise, shortening and the like.

The preparation of the PEP's of this invention may be achieved by direct esterification or by transesterification, although metal or base-catalyzed transesterification is preferred since direct esterification tends to char the oligosaccharides or polysaccharides. Methyl esters of the fatty acids are commercially available and may be reacted in the range of 50–200° C. in non-hydroxyl containing solvents, or in a self-solvent "melt" of the oligo or polysaccharide, in the appropriate molar quantities to provide the degree of esterification selected. Suitable catalysts are sodium methoxide, KOH, and titanium isopropoxide or tetraalkoxide. The reaction is cooled and the partially esterified polysaccharide separated and purified by conventional filtration. The transesterification can also be effected by yeast culture enzymes or esterases.

It should be understood that "polysaccharide" as used in the abbreviation is intended to cover both relatively low molecular weight polysaccharides and oligosaccharides, with the latter preferred. The very long chain (high polymer) polysaccharide starches and starch extracts, such as amylose are excluded from this definition. Further, the $C_5$ and $C_6$ saccharides are preferred.

Xantham gum maybe transesterified with palmitic acid methyl ester by the procedure described above to produce a PEP having a degree of esterification on the order of 35–60% depending on the mole ratio of reactants employed. The resulting fat product should have a good "mouth feel" and may be substituted for Crisco or other conventional fat in a variety of food formulations and for cooking, e.g. frying.

Likewise, guar gum, gum arabic, alginates, hydroxypropyl cellulose, cellulose or starch hydrolysis products, casein, karaya gum and pectin, all having $n=3$–50 units, may be transesterified with $C_3$–$C_{28}$ methyl esters in the range of 1–80% substitution of available hydroxyls to produce PEP's of this invention.

It should be understood that various modifications within the scope of this invention can be made by one of ordinary skill in the art without departing from the spirit thereof. I therefore wish my invention to be defined by the scope of the appended claims as broadly as the prior art will permit, and in view of the specification if need be.

What is claimed:

1. Partially esterified polysaccharides (PEPs) of the formula $[P-O(R)_x]_n$ having the structure:

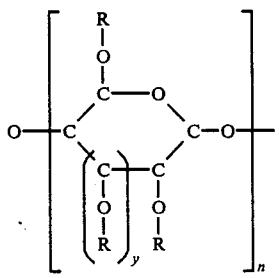

where P is a polysaccharide, n has an average value in the range of 3–50, y is 0–4, R is H or a same or different $C_{3-28}$ acyl moiety, and x is the degree of esterification ranging from 1–80 percent and is selected sufficient that the PEPs are resistant to digestive tract hydrolysis and absorption and exhibit properties ranging from oils through fats to greases.

2. Partially esterified polysaccharides as in claim 1 wherein the polysaccharide is an oligosaccharide of n=3–10.

3. Partially esterified polysaccharides as in claim 2 wherein the oligosaccharide is selected from xanthan gum, guar gum, gum arabic, aliginates, cellulose hydrolysis products, starch hydrolysis products, hydroxypropyl cellulose, casein, Karaya gum, pectin, and mixtures thereof.

4. Partially esterified polysaccharides as in claim 3 wherein the acyl moieties are selected from one or more $C_8$–$C_{24}$ acyls which may be the same or different in each PEP.

5. Partially esterified polysaccharides as in claim 4 wherein y is 1 or 2.

6. Partially esterified polysaccharides as in claim 5 wherein n, x, y and R are selected to impart a lipase hydrolysis rate of below about 20% as compared to olive oil.

7. Partially esterified polysaccharides as in claim 4 wherein n, x, y and R are selected to impart a lipase hydrolysis rate of below about 20% as compared to olive oil.

8. Partially esterified polysaccharides as in claim 3 wherein y is 1 or 2.

9. Partially esterified polysaccharides as in claim 2 wherein the acyl moieties are selected from one or more $C_8$–$C_{24}$ acyls which may be the same or different in each PEP.

10. Partially esterified polysaccharides as in claim 9 wherein y is 1 or 2.

11. Partially esterified polysaccharides as in claim 2 wherein y is 1 or 2.

12. Partially esterified polysaccharides as in claim 1 wherein y is 1 or 2.

13. Partially esterified polysaccharides as in claim 1 wherein n, x, y and R are selected to impart a lipase hydrolysis rate of below about 20% as compared to olive oil.

14. A low calorie food composition containing fat-type organoleptic ingredients, comprising fat ingredients and non-fat ingredients, wherein from about 10 to 100% of the total fat-type ingredients comprises at least one partially esterified polysaccharide as in claim 1.

15. A food composition as in claim 14 wherein n is selected to impart a lipase hydrolysis rate of below about 20% compared to olive oil.

16. A low calorie food composition containing fat-type organoleptic ingredients, comprising fat ingredients and non-fat ingredients, wherein from about 10 to 100% of the total fat-type ingredients comprises at least one partially esterified polysaccharide as in claim 4.

17. A food composition as in claim 16 wherein n is selected to impart a lipase hydrolysis rate of below about 20% compared to olive oil.

18. A low calorie food composition containing fat-type organoleptic ingredients, comprising fat ingredients and non-fat ingredients, wherein from about 10 to 100% of the total fat-type ingredients comprises at least one partially esterified polysaccharide as in claim 5.

19. A food composition as in claim 18 wherein n is selected to impart a lipase hydrolysis rate of below about 20% compared to olive oil.

20. A low calorie food composition containing fat-type organoleptic ingredients and non-fat ingredients, wherein from about 10 to 100% of the total fat-type ingredients comprise at least one partially esterified polysaccharide as in claim 3, n is selected to impart a lipase hydrolysis rate of below about 20% compared to olive oil, R is of sufficient length to be resistant to digestive tract absorption, and y is 1 or 2.

* * * * *